(12) United States Patent
Lesch, Jr.

(10) Patent No.: US 7,503,907 B1
(45) Date of Patent: Mar. 17, 2009

(54) MEDICAMENT CARTRIDGE AND INJECTION DEVICE

(75) Inventor: Paul R. Lesch, Jr., Lexington, MN (US)

(73) Assignee: Antares Pharma, Inc., Minneapolis, MN (US)

( * ) Notice: Subject to any disclaimer, the term of this patent is extended or adjusted under 35 U.S.C. 154(b) by 0 days.

(21) Appl. No.: 09/692,123

(22) Filed: Oct. 20, 2000

Related U.S. Application Data (60) Provisional application No. 60/160,895, filed on Oct. 22, 1999.

(51) Int. Cl.
   *A61M 5/00* (2006.01)
(52) U.S. Cl. .................................................. 604/232
(58) Field of Classification Search ............... 604/82, 604/89–91, 88, 232, 201, 191, 210, 181, 604/187, 272, 206, 226, 228, 266, 903, 152, 604/151, 131, 200, 202, 156, 205; 202/237
See application file for complete search history.

(56) References Cited

U.S. PATENT DOCUMENTS

| | | | |
|---|---|---|---|
| 1,288,174 A | 12/1918 | Pittenger | |
| 2,688,967 A * | 9/1954 | Huber | 604/206 |
| 2,717,601 A | 9/1955 | Brown | |
| 2,728,341 A | 12/1955 | Roehr | 128/218 |
| 3,308,821 A | 3/1967 | Shields | 128/218 |
| 3,375,825 A | 4/1968 | Keller | 128/221 |
| 3,382,865 A | 5/1968 | Worral, Jr. | 128/2 |
| 3,464,412 A | 9/1969 | Schwartz | |
| 3,527,212 A | 9/1970 | Clark | 128/173 |
| 3,779,371 A | 12/1973 | Rovinski | 206/47 A |
| 3,811,441 A | 5/1974 | Sarnoff | 128/218 DA |
| 3,838,689 A | 10/1974 | Cohen | 128/218 M |
| 3,853,125 A | 12/1974 | Clark et al. | 128/173 H |
| 3,946,732 A | 3/1976 | Hurscham | 128/218 M |
| 4,031,892 A | 6/1977 | Hurschman | 128/218 M |

(Continued)

FOREIGN PATENT DOCUMENTS

DE         882 600         7/1953

(Continued)

*Primary Examiner*—Nicholas D Lucchesi
*Assistant Examiner*—Christopher D Koharski
(74) *Attorney, Agent, or Firm*—Winston & Strawn LLP (57) ABSTRACT

The present invention discloses a medicament cartridge for an injection device, such as a syringe or a jet injector. The medicament cartridge according to the present invention includes a tube having a lumen, a needle operatively associated with an end of the tube and having a piercing end extending into the lumen, a second stopper located within the lumen near the other end of the tube and moveable within the lumen, and a first stopper located within the lumen, covering the piercing end of the needle, and moveable within the lumen. Firing the injection device to commence an injection may move the second stopper toward the needle, which compresses medicament located in the lumen between the first stopper and the second stopper. The compression of the medicament moves the first stopper into contact with the piercing end of the needle so that the piercing end pierces the first stopper to thereby create a fluid pathway for the medicament through the needle. Other methods of piercing the first stopper are anticipated as a means of activating the injection device. The disclosed medicament cartridge can be safely and aseptically manufactured and filled during assembly and, once manufactured and filled, eliminates contact between the medicament and the needle during storage.

29 Claims, 4 Drawing Sheets

U.S. PATENT DOCUMENTS

| | | | | |
|---|---|---|---|---|
| 4,051,850 A | 10/1977 | Tischlinger | ................ | 128/218 |
| 4,067,333 A * | 1/1978 | Reinhardt et al. | ........... | 604/191 |
| 4,072,149 A | 2/1978 | Tischlinger | ................ | 128/218 |
| 4,171,698 A | 10/1979 | Genese | ....................... | 128/218 |
| 4,258,713 A * | 3/1981 | Wardlaw | ..................... | 604/139 |
| 4,328,802 A | 5/1982 | Curley et al. | ............. | 128/272.1 |
| 4,573,971 A * | 3/1986 | Kamstra | .................... | 604/191 |
| 4,774,772 A | 10/1988 | Vetter et al. | | |
| 4,818,517 A * | 4/1989 | Kwee et al. | ................ | 424/488 |
| 4,820,286 A * | 4/1989 | van der Wal | ................ | 604/134 |
| 4,863,427 A | 9/1989 | Cocchi | ....................... | 604/110 |
| 4,874,381 A | 10/1989 | Vetter | ......................... | 604/191 |
| 4,950,240 A | 8/1990 | Greenwood et al. | ......... | 604/191 |
| 4,968,299 A | 11/1990 | Ahlstrand et al. | ............ | 604/90 |
| 4,968,302 A * | 11/1990 | Schluter et al. | ............ | 604/135 |
| 5,000,737 A | 3/1991 | Free et al. | .................. | 604/110 |
| 5,066,280 A | 11/1991 | Braithwaite | ................ | 604/110 |
| 5,069,670 A | 12/1991 | Vetter et al. | | |
| 5,080,649 A | 1/1992 | Vetter et al. | | |
| 5,102,388 A * | 4/1992 | Richmond | ................... | 604/88 |
| 5,137,528 A | 8/1992 | Crose | ......................... | 604/415 |
| 5,139,490 A * | 8/1992 | Vetter et al. | ................. | 604/201 |
| 5,185,985 A | 2/1993 | Vetter et al. | | |
| 5,226,882 A | 7/1993 | Bates | ......................... | 604/110 |
| 5,263,934 A * | 11/1993 | Haak | .......................... | 604/110 |
| 5,290,228 A | 3/1994 | Uemura | ....................... | 604/90 |
| 5,298,024 A | 3/1994 | Richmond | ................... | 604/90 |
| 5,320,603 A | 6/1994 | Vetter et al. | | |
| 5,352,203 A | 10/1994 | Vallelunga et al. | .......... | 604/110 |
| RE34,845 E | 1/1995 | Vetter et al. | | |
| 5,415,648 A * | 5/1995 | Malay et al. | ................ | 604/181 |
| 5,435,076 A | 7/1995 | Hjertman et al. | ............. | 34/296 |
| 5,472,422 A | 12/1995 | Ljungquist | ................... | 604/89 |
| 5,501,673 A | 3/1996 | Hjertman et al. | ............ | 604/191 |
| 5,549,561 A * | 8/1996 | Hjertman | .................... | 604/131 |
| 5,605,542 A * | 2/1997 | Tanaka et al. | ................. | 604/89 |
| 5,637,100 A * | 6/1997 | Sudo | .......................... | 604/238 |
| 5,716,338 A | 2/1998 | Hjertman et al. | ............. | 604/89 |
| 5,865,799 A * | 2/1999 | Tanaka et al. | ................. | 604/89 |
| 6,004,298 A | 12/1999 | Levander | .................... | 604/211 |
| 6,056,716 A | 5/2000 | D'Antonio et al. | ............ | 604/68 |
| 6,223,408 B1 | 5/2001 | Vetter et al. | | |

FOREIGN PATENT DOCUMENTS

GB              1181037        5/1968

* cited by examiner

MEDICAMENT CARTRIDGE AND INJECTION DEVICE

CROSS-REFERENCE TO RELATED APPLICATIONS

The benefit of Provisional Application No. 60/160,895 filed on Oct. 22, 1999 is claimed under 35 U.S.C. § 119(e).

FIELD OF THE INVENTION

The present invention is directed to a device for delivery of medicament, and in particular to an medicament cartridge and injection system.

BACKGROUND OF THE INVENTION

Liquid pharmaceutical preparations exist which contain insoluble or particulate constituents. This can be due to the insolubility of the drug in the vehicle in which it is stored. Alternatively, this can be due to the formulation of the drug to purposely render it relatively insoluble allowing the drug to be released over extended periods of time once it is injected. As a result, the insoluble or particulate constituents in the liquid pharmaceutical preparations separate upon storage, even over short periods of time.

In addition, these pharmaceutical preparations are typically packaged in cartridges or pre-filled syringes as the final drug container. There are a number of well known reasons for packaging the drugs in pre-filled syringes or cartridges ranging from economic efficiency to ease of use and administration. However, the inherent nature of these containers makes it difficult to resuspend the settled material since a cartridge or pre-filled syringe generally has a smaller volume of area in which to accomplish the resuspension than what one would normally find in a vial or ampule. As a result, the needle to be used for delivering the medication can become clogged if the suspensions are inadequately resuspended.

This potential for a clogged needle is particularly problematic in cases when the liquid pharmaceutical preparation containing insoluble particles is self administered or administered in the home by non-professional care givers. Ordinarily, when these liquid pharmaceutical preparations are administered in the hospital or other health care providing institutions by trained staff, one can rely on adequate handling of the medication despite settled material and plugged needles ensuring proper drug delivery. However when such pharmaceutical preparations are self administered or administered in the home by non-professional care givers, the risk for inadequate handling of the medication increases since the injection of such formulations requires that the administrator be able to adequately resuspend any settled material and clear the needle to ensure proper drug delivery.

SUMMARY OF THE INVENTION

The present invention relates to a medicament cartridge for an injection device, such as a jet injector for delivering any liquid based medicament, even those that contain particulate or insoluble constituents. The medicament cartridge according to the present invention comprises a tube having first and second ends and a lumen with a longitudinal axis for retaining the medicament therein, a needle operatively associated with the second end of the tube and having a piercing end, a second stopper located within the lumen near the first end of the tube and moveable within the lumen along the longitudinal axis, and a first stopper located within the lumen near the second end of the tubular member and moveable within the lumen along the longitudinal axis and covering the piercing end of the needle. Relative movement between the first stopper and the second stopper compresses the medicament and relative movement between the first stopper and the needle pierces the first stopper to create a fluid pathway for the medicament through the needle.

In one embodiment, the relative movement between the first stopper and the needle and relative movement between the first stopper and the second stopper results from the second stopper moving toward the second end of the tube. The needle is operatively associated with the second end of the tube with the piercing end extending from the second end of the tube into the lumen. The piercing end of the needle can be beveled to facilitate puncturing the first stopper.

In an exemplary embodiment, the first stopper has a cavity with a dimple, or equivalent thereof, and a narrow cross-section for ease of penetration and the second stopper is configured and dimensioned to mate with the shape of the first stopper to minimize the volume of the medicament remaining in the lumen after the injection is completed. The shape of the cavity in the first stopper can be frustroconical or any other suitable configuration. The needle can have an injecting tip opposite the piercing end and the injecting tip can be beveled to facilitate the injection process.

In another embodiment, the medicament cartridge further comprises an additional member that is operatively associated with the second end of the tube and the needle wherein relative movement of the second stopper toward the second end of the tube moves the entire tube into the member to allow the piercing end of the needle to pierce the first stopper and create the fluid pathway for the medicament through the needle.

In another embodiment, the lumen of the medicament cartridge has a portion with an enlarged diameter and further comprises a third stopper within the lumen located between the second stopper and the enlarged diameter and moveable within the lumen along the longitudinal axis. Typically, a first medicament component is present between the second and third stoppers, and a second medicament component is present between the third and first stoppers, such that, movement of the third stopper into the enlarged diameter portion of the lumen allows the first and second medicament components to mix to form the medicament.

DESCRIPTION OF THE PREFERRED EMBODIMENTS

Figure 1:
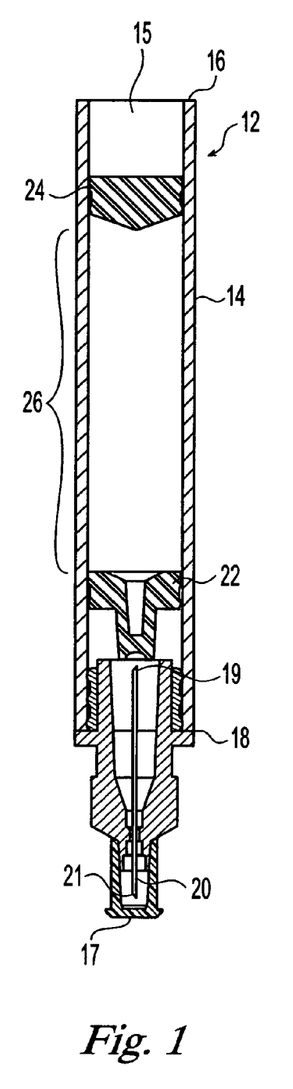
FIG. 1 shows a cross-sectional view of a first embodiment of a medicament cartridge according to the present invention.

As shown in FIG. 1, a first embodiment of a medicament cartridge 12 according to the present invention comprises a tube 14 with a distal or first end 16 and a proximal or second end 18. The terms proximal and distal are used with respect to the injection site so that the distal or first end 16 is the end of tube 14 farthest from the injection site and the proximal or second end 18 is nearest to the injection site. Tube 14 defines a lumen 15 that has a cylindrical shape and a longitudinal axis. When medicament cartridge 12 is filled with medicament, lumen 15 will be in contact with the medicament. Therefore, tube 14 should be made of a material compatible with the medicament. Alternatively, the walls of lumen 15 could be coated with such a material. An example of a material known to be compatible with most medicaments is borosilicate glass and other examples of suitable materials are well known to those of ordinary skill in the art. The medicament in contact with lumen 15, will typically be any liquid or fluid based pharmaceutical preparation, even those that contain insoluble or particulate components.

A needle 20 is operatively associated with second end 18 of tube 14. Needle 20 has a piercing end 19 that extends into lumen 15 and, in an exemplary embodiment, an injecting tip 21 extending beyond second end 18 of tube 14 that can be inserted into the person receiving the injection. The length of injecting tip 21 can be selected based on the particular application that medicament cartridge 12 is intended to be used in. Also, in an exemplary embodiment, the piercing end 19 and injecting tip 21 of needle 20 can be beveled.

As is the case with most medicament cartridges, a sheath or needle cap 17 typically covers injecting tip 21 to keep it clean and free from debris. Prior to use, needle cap 17 is removed. Medicament cartridge 12 also has a first stopper 22 located near the second end 18 of tube 14 and a second stopper 24 located near the first end 16 of tube 14. The medicament in lumen 15 is located between first stopper 22 and second stopper 24 in chamber 26, where chamber 26 is defined as the area of lumen 15 located between first stopper 22 and second stopper 24. In an exemplary embodiment, first stopper 22 has a cavity shown as a frustroconical shape with a dimple (but other designs are anticipated) and narrow cross-section for ease of penetration and second stopper 24 is configured and dimensioned to mate with the frustroconical shape of first stopper 22 to minimize the volume of the medicament remaining in chamber 26 after the injection is completed.

The present invention encompasses any manner of causing first stopper 22 to contact piercing end 19 of needle 20 to create a fluid pathway. For example, piercing of first stopper 22 could be caused by movement of needle 20 towards first end 16 of tube 14 by twisting or pushing needle 20 toward first stopper 22 thereby causing penetration of first stopper 22. The following show other methods of piercing first stopper 22 with piercing end 19 of needle 20 thereby creating a fluid pathway.

Figure 2:
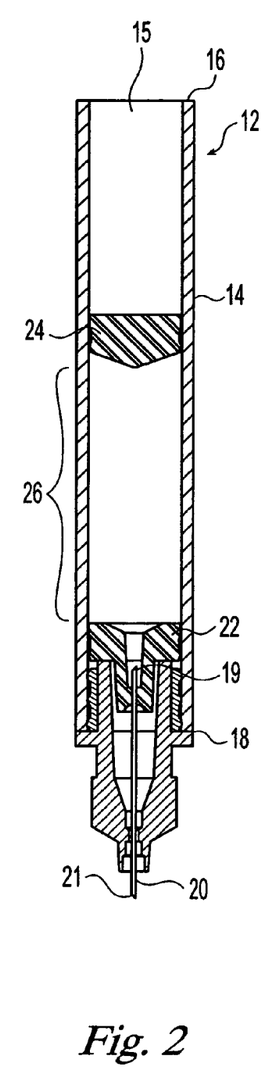
FIG. 2 shows a cross-sectional view of the medicament cartridge of FIG. 1 after injection firing process to commence an injection.
Figure 3:
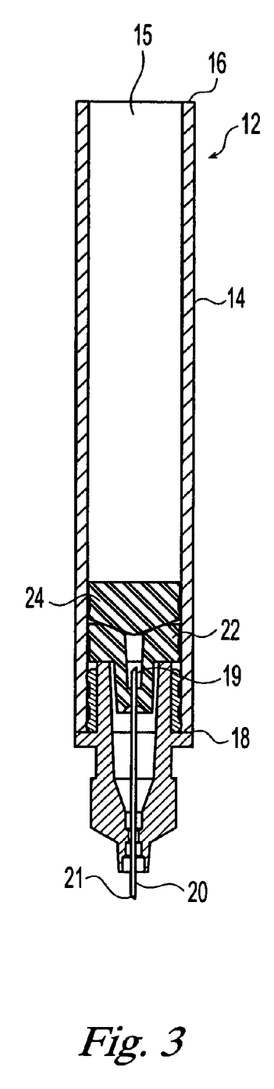
FIG. 3 shows a cross-sectional view of the medicament cartridge of FIG. 2 after completion of the injection.

FIGS. 2 and 3 show cross-sectional views of medicament cartridge 12 during firing. The injection firing process applies a force to second stopper 24 which may commence the injection firing process that results in a force being applied to second stopper 24 located near first end 16 of tube 14 urging second stopper 24 in the direction of second end 18 of tube 14. The movement of second stopper 24 in the direction of second end 18 causes compression of the medicament in chamber 26. As the medicament is incompressible to at least some degree, the compression of the medicament results in a force building up on first stopper 22. This force continues to build until first stopper 22 begins to move. At that time, first stopper 22, second stopper 24 and the medicament, located in chamber 26, move towards the second end 18 of tube 14. This array of first stopper 22, medicament, and second stopper 24 move as one unit until first stopper 22 comes in contact with the piercing end 19 of needle 20. Piercing end 19 of needle 20 pierces first stopper 22 creating a fluid pathway for the medicament. First stopper 22 ceases to move while second stopper 24 continues to respond to the force exerted on it and moves toward second end 18 of tube 14 until all the medicament located in chamber 26 is expelled. Since needle 20 is not introduced to the medicament located in chamber 26 until the latter end of the firing process, any insoluble or particulate constituents in the medicament that may be present cannot settle on needle 20 thereby eliminating any possibilities of needle 20 becoming clogged before firing. Also, there is no need to agitate the cartridge to try to mix or re-suspend the particulate matter because it does not contact the needle until the injection device is fired.

Figures 4, 5:
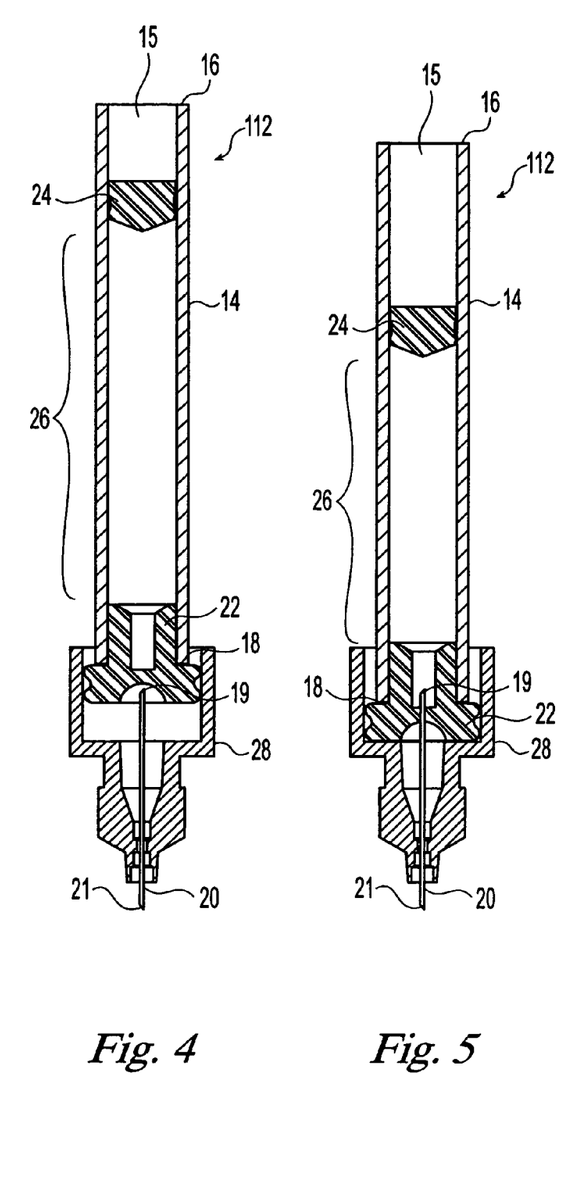
FIG. 4 shows a cross-sectional view of a second embodiment of the medicament cartridge according to the present invention.
FIG. 5 shows a cross-sectional view of the medicament cartridge of FIG. 4 after injection firing process to commence an injection.

FIG. 4 shows a cross-sectional view of a second embodiment of the medicament cartridge 112 according to the present invention. In general, most of the structure of medicament cartridge 112 is like or comparable to the structure of medicament cartridge 12. Accordingly, the same reference numeral is used for like components and discussion of these components is not believed necessary. However, unlike medicament cartridge 12, medicament cartridge 112 operatively associates needle 20 to member 28 and member 28 is operatively associated with tube 14 where second end 18 of tube 14 is comprised of first stopper 22.

Figure 6:
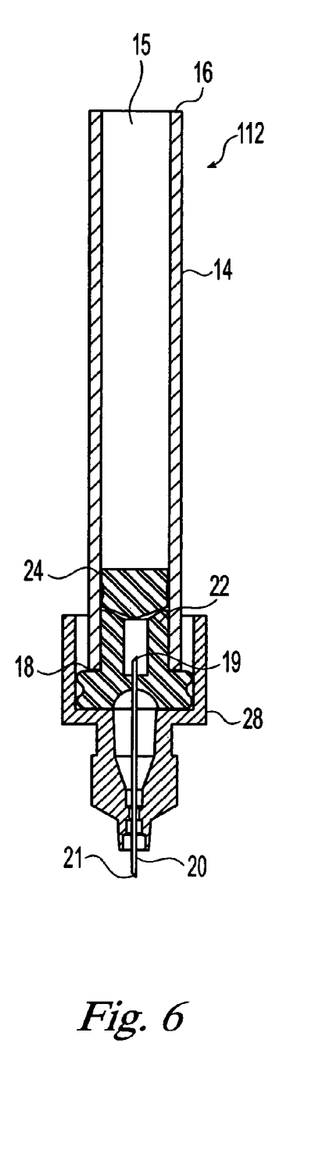
FIG. 6 shows a cross-sectional view of the medicament cartridge of FIG. 5 after completion of the injection.

FIGS. 5 and 6 show cross-sectional views of medicament cartridge 112 during firing. The injection firing process commences as a force applied to medicament cartridge 112 causes relative movement between member 28 and tube 14. This relative movement causes first stopper 22 to be pierced by piercing end 19 of needle 20 thereby creating a fluid pathway for the medicament. If the force causing the relative movement was not applied to second stopper 24, then a separate force is applied to second stopper 24 causing it to move in the direction of second end 18 of tube 14 ejecting all the medicament located in chamber 26, which is defined as the area of lumen 15 between first stopper 22 and second stopper 24, through needle 20. Since needle 20 is not introduced to the medicament located in chamber 26 until the firing process has begun, any insoluble or particulate constituents in the pharmaceutical preparation that may be present cannot settle on needle 20 thereby eliminating any possibilities of needle 20 becoming clogged before firing. Also, there is no need to agitate the cartridge to try to mix or re-suspend the particulate matter because it does not contact the needle until the injection device is fired.

Figure 7:
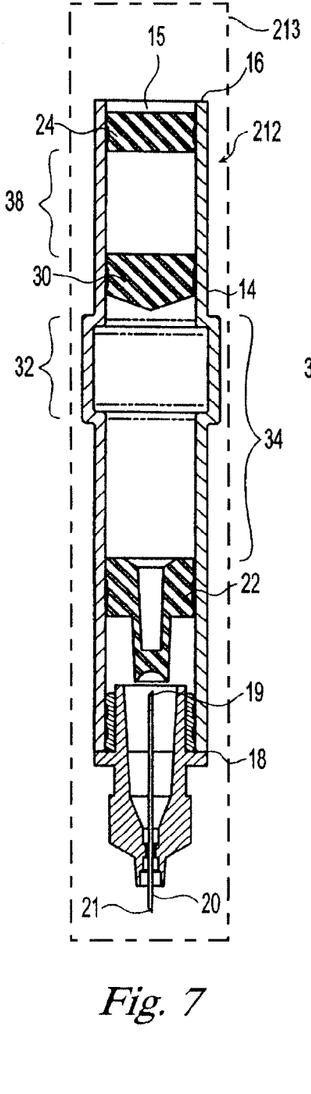
FIG. 7 shows a cross-sectional view of another embodiment of the medicament cartridge schematically shown in an injection device according to the present invention with the medicament cartridge having two chambers.

FIG. 7 shows a cross-sectional view of another embodiment of medicament cartridge 212 used in a jet injector 213 according to the present invention. In general, most of the structure of medicament cartridge 212 is like or comparable to the structure of medicament cartridges 12, 112. Accordingly, the same reference numeral is used for like components. Medicament cartridge 212 comprises a tube 14 with a distal or first end 16 and a proximal or second end 18 wherein tube 14 defines a lumen 15 that has a cylindrical shape and a longitudinal axis. A portion of lumen 15 has an enlarged diameter which is designated as bypass 32.

A needle 20 is operatively associated with second end 18 of tube 14. Needle 20 has a piercing end 19 that extends into lumen 15 and, in an exemplary embodiment, an injecting tip 21 extending beyond second end 18 of tube 14 that can be inserted into the person receiving the injection. The length of injecting tip 21 can be selected based on the particular application that medicament cartridge 212 is intended to be used in.

Medicament cartridge 212 also has a first stopper 22 located near second end 18 of tube 14, a second stopper 24 located near first end 16 of tube 14, and a third stopper 30 located between second stopper 24 and bypass 32. The medicament in lumen 15 is located between second stopper 24 and third stopper 30 in first chamber 38, where first chamber 38 is defined as the area of lumen 15 located between second stopper 24 and third stopper 30, and between third stopper 30 and first stopper 22 in second chamber 34, where second chamber 34 is defined as the area of lumen 15 located between first stopper 22 and third stopper 30. First chamber 38 usually contains a particulate, insoluble or colloidal medicament component and second chamber 34 usually contains a liquid or diluent medicament component.

Figure 8:
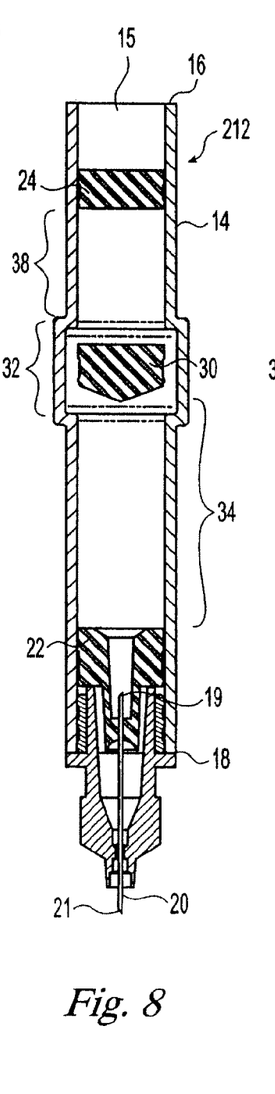
FIG. 8 shows a cross-sectional view of the medicament cartridge of FIG. 7 after injection firing process to commence an injection.
Figure 9:
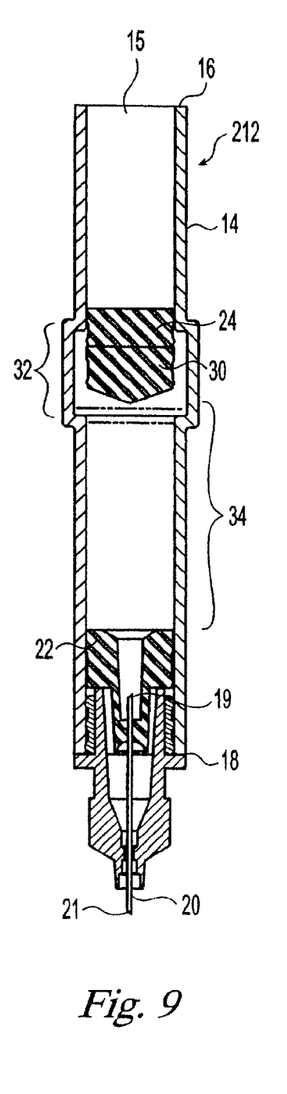
FIG. 9 shows a cross-sectional view of the medicament cartridge of FIG. 8 when the upper stopper has reached the bypass completely expelling the contents of the upper chamber into the lower chamber.
Figure 10:
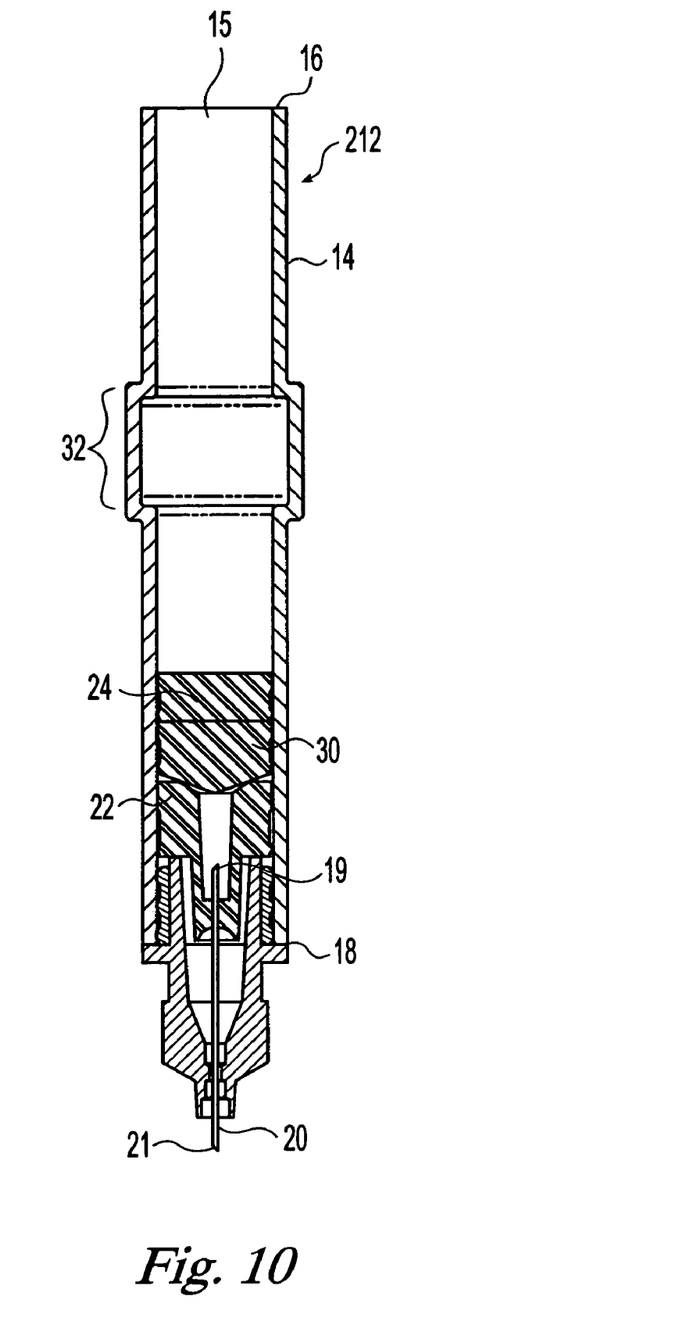
FIG. 10 shows a cross-sectional view of the medicament cartridge of FIG. 9 after completion of the injection.

FIGS. 8, 9 and 10 show cross-sectional views of medicament cartridge 212 during firing. The injection firing process commences by a force being applied to second stopper 24 located at first end 16 of tube 14 urging second stopper 24 in the direction of second end 18 of tube 14. The movement of second stopper 24 in the direction of second end 18 causes compression of the medicament in first chamber 38. As the medicament is incompressible to at least some degree, the compression of the medicament results in a force building up on third stopper 30. This force continues to build until third stopper 30 begins to move. At that time, second stopper 24, third stopper 30 and the medicament, located in first chamber 38, move towards the second end 18 of tube 14. This array of second stopper 24, medicament located in first chamber 38, and third stopper 30 continues to move as one unit until third stopper 30 reaches bypass 32. At that time, third stopper 30 ceases to move while second stopper 24 continues to respond to the force exerted on it and moves toward second end 18 of tube 14 expelling all the medicament located in first chamber 38 into second chamber 34 via bypass 32. By forcing the medicament through the bypass and into the diluent, it is resuspended and diluted for injection. As force continues to be applied to second stopper 24, second stopper 24 and third stopper 30 respond by moving toward second end 18 of tube 14. The movement of second 24 and third 30 stoppers in the direction of second end 18 causes compression of the medicament in second chamber 34. As the medicament is incompressible to at least some degree, the compression of the medicament results in a force building up on first stopper 22. This force continues to build until first stopper 22 begins to move. At that time, first stopper 22, second 24 and third 30 stoppers and the medicament, located in second chamber 34, move towards the second end 18 of tube 14. This array of first stopper 22, medicament, and second 24 and third 30 stoppers move as one unit until first stopper 22 comes in contact with piercing end 19 of needle 20. Piercing end 19 of needle 20 pierces first stopper 22 creating a fluid pathway for the medicament. First stopper 22 ceases to move while second 24 and third 30 stoppers continue to respond to the force exerted on them and move toward second end 18 of tube 14 until all the medicament located in second chamber 34 is expelled. Since needle 20 is not introduced to the medicament located in chamber 26 until the latter end of the firing process, any insoluble or particulate constituents in the medicament that may be present cannot settle on needle 20 thereby eliminating any possibilities of needle 20 becoming clogged before firing.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An injector, comprising:
    a medicament cartridge comprising:
        a medicament;
        a tube having first and second ends and a lumen with a longitudinal axis for retaining the medicament therein;
        a needle fixed in a hub received within the tube, such that the needle is operatively associated with the second end of the tube, the needle having a piercing end extending into the lumen;
        a first stopper located at a first position near the second end moveable within the lumen along the longitudinal axis, the first stopper having a proximal portion in sealing contact against the tube in the lumen and a distal portion protruding distally from the proximal portion and spaced from tube in the lumen, the distal portion being disposed and configured to be pierced by the piercing end of the needle and to be received within the hub when pierced by the piercing end of the needle; and
        a second stopper within and against the tube in the lumen located at a second position near the first end moveable within the lumen along the longitudinal axis,
        wherein movement of the first stopper with respect to the tube from the first position toward the needle causes the piercing end of the needle to pierce the first stopper to create a fluid pathway for the medicament through the needle, and movement of the second stopper with respect to the tube from the second position toward the second end of the tube compresses the medicament held between the second stopper and the first stopper so that the medicament is expelled through the fluid pathway;
    wherein the injector is a jet injector.

2. The injector of claim 1, wherein movement of the second stopper toward the second end of the tube compresses the medicament between the first stopper and the second stopper to move the first stopper toward the second end of the tube to allow the piercing end of the needle to pierce the first stopper and create the fluid pathway for the medicament through the needle.

3. The injector of claim 1, wherein the piercing end of the needle has a bevel.

4. The injector of claim 1, wherein the needle has an injecting tip extending beyond the second end of the tube.

5. The injector of claim 4, wherein the injecting tip of the needle has a bevel and is configured for insertion into a patient who is receiving the injection.

6. The injector of claim 1, wherein the tube is cylindrical.

7. The injector of claim 1, wherein the lumen has a portion with an enlarged diameter, and further comprising a third stopper within the lumen located between the second stopper and the enlarged diameter and moveable within the lumen along the longitudinal axis into the large diameter for providing a bypass for the medicament disposed between the second and third stoppers to pass to a chamber between the third and first stoppers.

8. The jet injector of claim 7, wherein the third stopper is configured for moving past the enlarged diameter towards the first stopper for injecting the medicament that passed from between the third and second stoppers together with the medicament between the third and first stoppers.

9. The injector of claim 1, wherein the first stopper has a frustroconical shape.

10. The injector of claim 9, wherein the second stopper has a medicament contacting surface configured and dimensioned to mate with the frustroconical shape of the first stopper to minimize volume of medicament remaining in the lumen after the injection is completed.

11. The injector of claim 1, wherein the first stopper has a dimple and narrow cross-section where the needle penetrates the first stopper.

12. The injector of claim 1, wherein the lumen has a cylindrical shape.

13. The injector of claim 1, wherein the cartridge is configured for use in combination with an injection device for firing the cartridge to expel the medicament.

14. The injector of claim 1, further comprising an injection device configured for firing the cartridge to expel the medicament.

15. The jet injector of claim 1, wherein the jet injector is configured for jet injection of the medicament from the fluid pathway.

16. The jet injector of claim 1, wherein the first stopper is configured to substantially prevent any of the medicament contained in the cartridge from contacting the needle prior to the firing of the jet injector.

17. The injector of claim 16, wherein the medicament is a liquid pharmaceutical preparation containing insoluble particles.

18. The jet injector of claim 16, wherein the first stopper is slideable within the tube.

19. The jet injector of claim 16, wherein the medicament cartridge comprises only the two stoppers that contain all of the medicament therebetween.

20. The jet injector of claim 1, wherein the medicament cartridge is configured such that all of the medicament in the cartridge is injected together.

21. The jet injector of claim 1, wherein the needle is in fixed association with the second end of the tube prior to firing the injector, and the first stopper is free of any device to puncture another of the stoppers.

22. A jet injector, comprising:
a medicament cartridge comprising:
a medicament comprising first and second medicament components;
a tube having first and second ends and a lumen with a longitudinal axis for retaining the medicament therein, wherein the lumen has a portion with an enlarged diameter;
a needle fixed in a hub received within the second end of the tube and having a piercing end extending into the lumen;
a first stopper within the lumen located near the second end moveable within the lumen along the longitudinal axis, the first stopper having a proximal portion in sealing contact against the tube in the lumen and a distal portion protruding distally from the proximal portion and spaced from tube in the lumen and disposed and configured to be pierced by the piercing end of the needle, wherein the distal portion of the first stopper is configured to be received within the hub when pierced by the piercing end of the needle;
a second stopper within the lumen located near the first end moveable within the lumen along the longitudinal axis; and
a third stopper within the lumen located between the second stopper and the enlarged diameter and moveable within the lumen along the longitudinal axis, wherein the first medicament component is disposed between the second and third stoppers, and the second medicament component is present between the third and first stoppers;
wherein movement between the first stopper and the needle causes the piercing end of the needle to pierce the first stopper to create a fluid pathway for the medicament through the needle and movement of the second stopper toward the second end of the tube compresses the medicament held between the second stopper and the first stopper so that the medicament is expelled through the fluid pathway;
wherein movement of the third stopper to the enlarged diameter portion allows the first and second medicament components to mix to form the medicament.

23. A method of injecting a medicament, comprising:
providing a medicament within a lumen of a tube in a jet injector, the tube having first and second ends and between first and second stoppers that are disposed near the second and first ends of the tube, respectively, the first stopper being positioned to substantially prevent any of the medicament in the cartridge from contacting a needle prior to firing of the jet injector, the needle being fixed in a hub at the second end, and the first stopper having a proximal portion in sealing contact against the tube in the lumen and a distal portion protruding distally from the proximal portion and spaced from tube in the lumen;
firing the jet injector for:
moving the first stopper within the lumen towards the needle to cause the distal portion to be received within the hub such that a piercing end of the needle pierces the distal portion to create a fluid pathway for the medicament through the needle, and
moving the second stopper within the lumen towards the second end to compress the medicament to expel the medicament through the fluid pathway in a jet injection.

24. The method of claim 23, wherein movement of the second stopper toward the second end of the tube compresses the medicament between the first stopper and the second stopper to move the first stopper toward the second end of the tube for piercing the first stopper with the piercing end of the needle and create the fluid pathway for the medicament through the needle.

25. The method of claim 23, wherein the medicament is expelled through an injecting tip of the needle that extends beyond the second end of the tube.

26. The method of claim 23, wherein:
a first medicament component of the medicament is provided between the second and a third stopper in the lumen;
a second medicament component is provided between the third and first stoppers in the lumen;
the second stopper is moved to move the third stopper by compressing the first medicament component, thereby moving the first stopper for piercing with the piercing end by compressing the second medicament component; and the first and second medicament components are mixed by moving the third stopper to an enlarged diameter portion of the lumen and moving second stopper to displace the first medicament to between the first and third stoppers.

27. The method of claim 23, wherein the cartridge that comprises the tube, needle, stoppers, and medicament, is fired by a jet injection device to inject the medicament.

28. A jet injector, comprising:
a medicament cartridge comprising:
   a medicament;
   a tube having first and second ends and a lumen with a longitudinal axis for retaining the medicament therein;
   a needle fixed in a hub at the second end of the tube and having a piercing end extending into the lumen;
   a first stopper within and against the lumen located at a first position near the second end moveable within the lumen along the longitudinal axis, the first stopper having a proximal portion in sealing contact against the tube in the lumen and a distal portion protruding distally from the proximal portion and spaced from tube in the lumen; and
   a second stopper within and against the lumen located at a second position near the first end moveable within the lumen along the longitudinal axis,
   wherein movement of the first stopper with respect to the tube from the first position toward the needle causes the distal portion of the first stopper to be received within the hub and to be pierced by the piercing end of the needle to create a fluid pathway for the medicament through the needle across the first stopper, and movement of the second stopper with respect to the tube from the second position toward the second end of the tube compresses the medicament held between the second stopper and the first stopper so that the medicament is expelled through the fluid pathway.

29. The jet injector of claim 28, wherein the needle is in fixed association with the second end of the tube prior to firing the injector.

* * * * *